United States Patent [19]

Harada et al.

[11] Patent Number: 4,928,701
[45] Date of Patent: May 29, 1990

[54] METHOD AND APPARATUS FOR MONITORING BLOOD PRESSURE

[75] Inventors: Chikao Harada; Minoru Niwa, both of Nagoya, Japan

[73] Assignee: Colin Electronics Co., Ltd., Aichi, Japan

[21] Appl. No.: 312,183

[22] Filed: Feb. 21, 1989

[30] Foreign Application Priority Data

Feb. 23, 1988 [JP] Japan .................................. 63-40248
Feb. 24, 1988 [JP] Japan .................................. 63-41677

[51] Int. Cl.$^5$ ............................................. A61B 5/02
[52] U.S. Cl. ..................................... 128/677; 128/681
[58] Field of Search .................. 128/672, 677–686, 128/687–690

[56] References Cited

U.S. PATENT DOCUMENTS 4,562,843  1/1986  Djordjevich et al. .......... 128/677 X
4,669,485  6/1987  Russell ............................. 128/677 X

*Primary Examiner*—Angela D. Sykes
*Attorney, Agent, or Firm*—Oliff & Berridge

[57] ABSTRACT

A method and apparatus for monitoring blood pressure of a subject, the method including the steps of continuously detecting pulse wave which is produced from an artery synchronously with heartbeat of the subject; the pulse wave consisting of a plurality of pulses, repetitively measuring blood pressure of the subject, each of the repetitive blood pressure measurements being effected by inflating a cuff set on a body portion and deflating the cuff; repetitively determining a relationship between blood pressure and magnitude of pulse wave, based on each of the repetitively measured blood pressures and magnitude of at least one pulse of the pulse wave which pulse is detected during a predetermined time length including a first time length immediately before beginning of the inflation of the inflatable cuff for a corresponding one of the repetitive blood pressure measurements, and a second time length following the first time length; replacing each of the repetitively determined relationships, with another relationship determined following the each of the repetitively determined relationships; and continuously determining blood pressure of the subject based on magnitude of each of the pulses of the continuously detected pulse wave according to a currently effective one of the repetitively determined and replaced relationships.

25 Claims, 5 Drawing Sheets

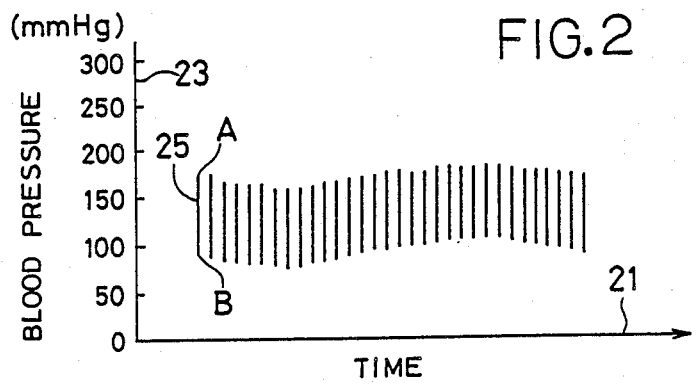
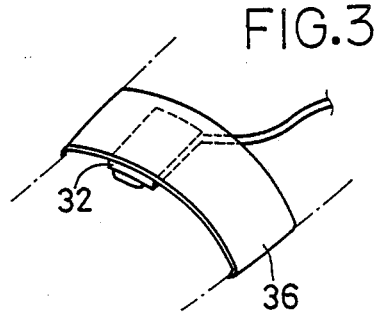
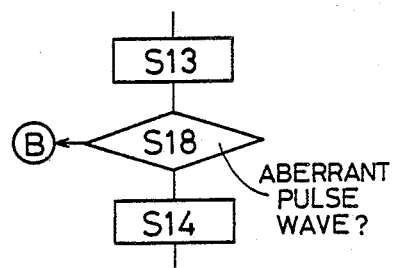
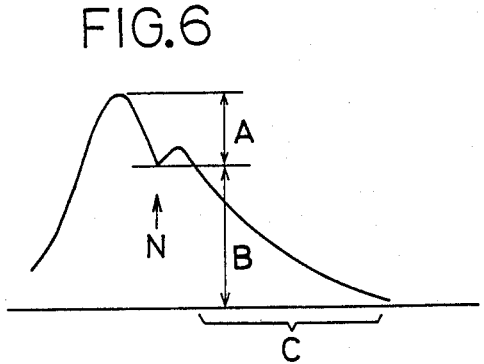
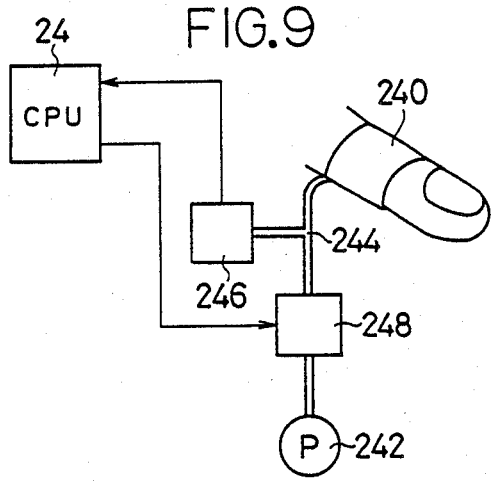

METHOD AND APPARATUS FOR MONITORING BLOOD PRESSURE

BACKGROUND OF THE INVENTION

1. Field of the Invention

The present invention relates to a method and apparatus for monitoring blood pressure of a living body based on pulse wave.

2. Related Art Statement

There is known the art of determining blood pressure based on pulse wave, i.e., pressure oscillation produced from an arterial vessel synchronously with heartbeat of a subject. The art consists of pressing a body portion of a subject with, for example, an inflatable cuff, detecting pressure oscillation transmitted to the cuff synchronously with heartbeat of the subject, and determining blood pressure based on variation in magnitude of the pressure oscillation, the magnitude variation of the pressure oscillation corresponding to magnitude variation of the pulse wave.

However, if the above-indicated blood pressure measuring method is applied to, for example, a patient who has just undergone a surgical operation and therefore must be monitored regarding blood pressure for a comparatively long time, the body portion of the patient on which the inflatable cuff is set is continuously pressed with a comparatively high pressing force of the cuff. Consequently the patient suffers from uncomfortable feeling and even congestion

SUMMARY OF THE INVENTION

It is therefore an object of the present invention to provide a method and an apparatus for monitoring blood pressure of a living body, which permits a blood pressure monitoring with extremely reduced uncomfortable feeling of the living body.

According to a first aspect of the present invention, there is provided a method of monitoring blood pressure of a subject, the method comprising the steps of (a) continuously detecting pulse wave which is produced from an arterial vessel of the subject synchronously with heartbeat of the subject, the pulse wave consisting of a plurality of pulses, (b) repetitively measuring blood pressure of the subject, each of the repetitive blood pressure measurements being effected by inflating an inflatable cuff set on a body portion of the subject so as to press the body portion, and subsequently deflating the inflatable cuff, (c) repetitively determining a relationship between blood pressure and magnitude of pulse wave, based on each of the repetitively measured blood pressures and magnitude of at least one pulse of the pulse wave which pulse is detected during a predetermined time length comprising a first time length immediately before beginning of the inflation of the inflatable cuff for a corresponding one of the repetitive blood pressure measurements, and a second time length following the first time length, (d) replacing each of the repetitively determined relationships, with another relationship determined following the each of the repetitively determined relationships, and (e) continuously determining blood pressure of the subject based on magnitude of each of the pulses of the continuously detected pulse wave, according to a currently effective one of the repetitively determined and replaced relationships.

In the blood pressure monitoring method arranged as described above, actual blood pressure is repetitively measured, and the relationship between pulse wave magnitude and blood pressure is repetitively determined based on each of the repetitively measured actual blood pressures and magnitude of at least one pulse of the pulse wave detected immediately before, or after, the beginning of the cuff inflation for measuring the each of the actual blood pressures. Each of the repetitively determined relationships is replaced with another following the each of the relationships. Consequently, blood pressure of the subject is continuously determined based on magnitude of each of pulses of the pulse wave continuously detected by the pulse wave sensor, according to a currently effective one of the repetitively determined and replaced relationships. Since the present method does not require a body portion of the subject to be continuously pressed, the method does not cause blood circulation of the subject to be occluded and extremely reduces uncomfortable feeling of the subject, even in a comparatively long continuous blood pressure monitoring.

In a preferred embodiment of the method of the present invention, the step of repetitively determining the relationship consists of determining the relationship at regular time intervals, the regular time interval falling in a range of 5 to 10 minutes.

In another embodiment of the method of the invention, each of the repetitively determined relationships is determined based on a corresponding one of the repetitively measured blood pressures and magnitude of a pulse of the pulse wave which pulse is detected, during the second time length, when pressure in the inflatable cuff is equal to the corresponding one of the repetitively measured blood pressures. In this case, the relationship between pulse wave magnitude and blood pressure is replaced with another determined immediately after measurement of each of the actual blood pressures. Therefore, each of the thus determined relationships reflects accurate correspondence between pulse wave magnitude and blood pressure. Accordingly, accurate blood pressure is estimated based on magnitude of each pulse of the pulse wave according to a currently effective one of the relationships. The second time length may be equal to a time length required for inflating and deflating the inflatable cuff for each of the repetitive blood pressure measurements.

In yet another embodiment of the first aspect of the invention, the method further comprises the step of selecting one of a first pulse group consisting of at least one pulse of the pulse wave detected during the first time length and a second pulse group consisting of at least one pulse of the pulse wave detected during the second time length, each of the repetitively determined relationships being determined based on a corresponding one of the repetitively measured blood pressures and magnitude of the at least one pulse of the selected one of the first and second pulse groups. For example, if a magnitude of the at least one pulse of the second pulse group is smaller more than a predetermined value than that of the at least one pulse of the first pulse group, the first pulse group is selected, while if otherwise the second pulse group is selected. In the case where the pulse wave sensor is set over a radial artery extending in the arm around which the cuff is wound and located on a peripheral or downstream side of the cuff, the at least one pulse of the second pulse group detected in the second time length, namely, after the beginning of the cuff inflation, has a comparatively small magnitude and a deformed wave form. Accordingly, the first pulse group detected immediately before the beginning of the cuff inflation is selected. Meanwhile, in the case where the pulse wave sensor is set over a radial artery extending in a free arm different from the cuff arm, the at least one pulse of the second pulse group has a magnitude comparable to that of the at least one pulse of the first pulse group, and therefore the second pulse group is selected. Thus, the present embodiment is capable of accurately determining the relationship between pulse wave magnitude and blood pressure, irrespective of the positional relationship between the pressure sensor and the inflatable cuff.

In the above embodiment of the method of the invention, it is preferred that each of the first and second time lengths be equal to a multiple time length of a time period of respiration of the subject. Also, it is preferred that the at least one pulse of each of the first and second pulse groups consists of eight pulses of the pulse wave. In the latter case, the each of the repetitively determined relationships may be determined based on the corresponding one of the repetitively measured blood pressures and an average of magnitudes of the eight pulses of the selected one of the first and second pulse groups.

In a further embodiment of the method of the invention, the relationship is expressed as follows:

$$B = K \cdot M + a$$

wherein
BP blood pressure,
M: magnitude of pulse wave, and
K, a: constants.

In another preferred embodiment of the method of the invention, the step of repetitively measuring blood pressure of the subject consists of repetitively measuring maximum and minimum blood pressure of the subject, and the step of continuously determining blood pressure of the subject consists of continuously determining maximum and minimum blood pressure based on a maximum and a minimum magnitude of each of the pulses of the pulse wave according to the currently effective relationship.

According to a second aspect of the present invention, there is provided an apparatus for monitoring blood pressure of a subject, the apparatus comprising: (1) a pulse wave sensor for continuously detecting pulse wave which is produced from an arterial vessel of the subject synchronously with heartbeat of the subject, the pulse wave consisting of a plurality of pulses, (2) blood pressure measuring means for repetitively measuring blood pressure of the subject, each of the repetitive blood pressure measurements being effected by inflating an inflatable cuff set on a body portion of the subject so as to press the body portion, and subsequently deflating the inflatable cuff, (3) first determining means for repetitively determining a relationship between blood pressure and magnitude of pulse wave, based on each of the repetitively measured blood pressures and magnitude of at least one pulse of the pulse wave which pulse is detected during a predetermined time length comprising a first time length immediately before beginning of the inflation of the inflatable cuff for a corresponding one of the repetitive blood pressure measurements, and a second time length following the first time length, the first determining means replacing each of the repetitively determined relationships, with another relationship following the each of the repetitively determined relationships, and (4) second determining means for continuously determining blood pressure of the subject based on magnitude of each of the pulses of the continuously detected pulse wave, according to a currently effective one of the repetitively determined and replaced relationships.

The blood pressure monitoring apparatus constructed as described above provides the same advantages of the blood pressure monitoring method according to the first aspect of the invention.

In a preferred embodiment of the apparatus of the present invention, the first determining means determines the relationship at regular time intervals, the regular time interval falling in a range of 5 to 10 minutes.

In another embodiment of the apparatus of the invention, the first determining means repetitively determines the relationship based on each of the repetitively measured blood pressures and magnitude of a pulse of the pulse wave which pulse is detected, during the second time length, when pressure in the inflatable cuff is equal to the each of the repetitively measured blood pressures.

In yet another embodiment of the apparatus of the invention, the first determining means selects one of a first pulse group consisting of at least one pulse of the pulse wave detected during the first time length and a second pulse group consisting of at least one pulse of the pulse wave detected during the second time length, and determines the relationship based on each of the repetitively measured blood pressures and magnitude of the at least one pulse of the selected one of the first and second pulse groups.

In the above embodiment of the second aspect of the invention, it is preferred that the apparatus further comprise first memory means for storing the at least one pulse of the first pulse group detected in the first time length, and second memory means for storing the at least one pulse of the second pulse group detected in the second time length, the first determining means selecting the first pulse group if magnitude of the at least one pulse of the second pulse group is smaller more than a predetermined value than magnitude of the at least one pulse of the first pulse group, and selecting the second pulse group if the magnitude of the at least one pulse of the second pulse group is not smaller more than the predetermined value than the magnitude of the at least one pulse of the first pulse group.

In a further embodiment of the second aspect of the invention, the apparatus further comprises means for judging that the currently effective one of the repetitively determined relationships has been broken, the blood pressure measuring means measuring another blood pressure of the subject and the first determining means replacing the broken relationship with another relationship determined based on the another blood pressure and magnitude of at least one pulse of the pulse wave detected in the first time length immediately before the beginning of the inflation of the inflatable cuff for measuring the another blood pressure, or magnitude of at least one pulse of the pulse wave detected in the second time length following the first time length.

In a still further embodiment of the second aspect of the invention, the apparatus further comprises a display device for displaying the continuously determined blood pressure of the subject, along a time axis.

BRIEF DESCRIPTION OF THE DRAWINGS

The above and optional objects, features and advantages of the present invention will be better understood by reading the following detailed description of the presently preferred embodiments of the invention, when considered in conjunction with the accompanying drawings, in which:

FIG. 2 is a graph showing a time-wise varying trend of blood pressure displayed by a display device of the apparatus of FIG. 1;

FIG. 3 is a view illustrating a pulse wave sensor of the apparatus of FIG. 1 set on a wrist of a subject;

FIG. 5 is a flow chart partly illustrating the operation of another embodiment of the apparatus of the invention;

FIG. 6 is a view showing the position of a notch N of a pulse of the pulse wave detected by the pulse wave sensor of FIG. 3, and a diastolic portion C of the pulse;

FIG. 9 is a view illustrating a pulse wave detecting device which is used in place of the pulse wave sensor of FIG. 3.

DETAILED DESCRIPTION OF THE PREFERRED EMBODIMENTS

Figure 1:
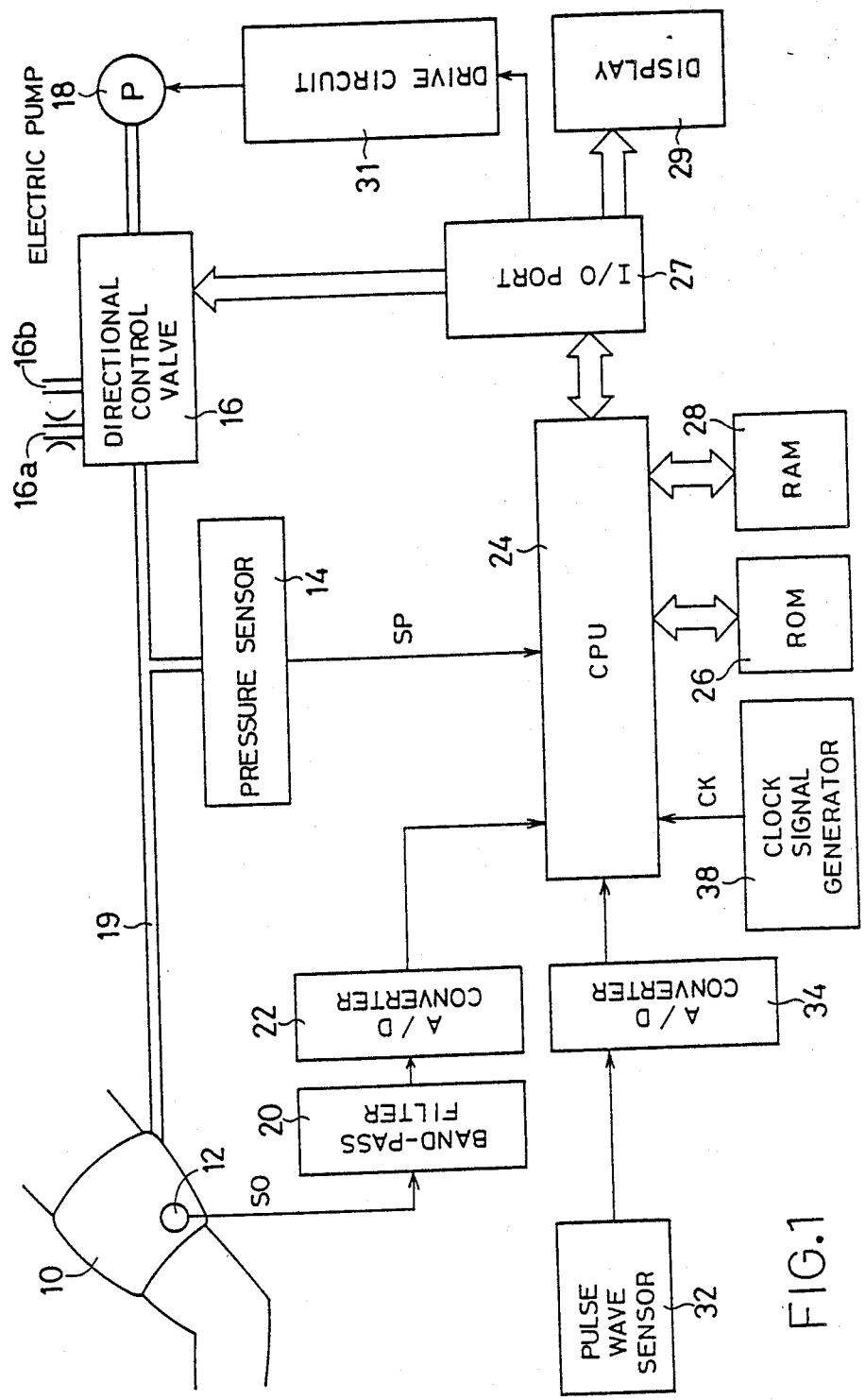
FIG. 1 is a diagrammatic view illustrating a blood pressure monitoring apparatus of the present invention.

Referring first to FIG. 1, there is illustrated a blood pressure monitoring apparatus embodying the present invention. In the figure, reference numeral 10 designates a bag-like inflatable cuff formed of rubber. The cuff 10 is wound around an upper arm of a subject so as to press the upper arm. In the bag of the cuff 10 there is disposed a microphone 12. The cuff 10 is connected via a piping 19 to a pressure sensor 14, a directional control valve 16 and an electrically operated pump 18.

The microphone 12 detects pulse sounds (i.e., Korotkoff sounds) produced from the upper arm, and generates pulse sound signal SO representing the detected Korotkoff sounds to a band pass filter 20. The band pass filter 20 selectively transmits signal component in a frequency range from 30 to 80 Hz. Pulse sound signal (component) SO transmitted through the band pass filter 20 is supplied to a CPU (central processing unit) via an A/D (analog-to-digital) converter 22.

The pressure sensor 14 detects pressure in the inflatable cuff 10 (hereinafter, referred to as cuff pressure P), and generates to the CPU 24 cuff pressure signal SP representing the detected cuff pressure P.

The directional control valve 16 disposed between the cuff 10 and the electric pump 18 is selectively placed in an inflation position, a slow deflation position and a rapid deflation position thereof, so as to regulate cuff pressure P. Specifically, while the control valve 16 is placed in the inflation position, both a slow and a rapid deflation port 16a, 16b of the valve 16 are closed, so that pressurized fluid such as pressurized air is supplied from the electric pump 18 to the cuff 10. Meanwhile, if cuff pressure P is increased to a predetermined target pressure level, the control valve 16 is switched from the inflation position to the slow deflation position in which the slow deflation port 16a having a restrictor is opened so as to decrease cuff pressure P at a predetermined slow rate suitable for effecting blood pressure measurement. Thus, in the present embodiment, while cuff pressure P is slowly decreased with the control valve 16 positioned in the slow deflation position, a blood pressure measurement is conducted. Cuff pressure P is rapidly decreased when the control valve 16 is placed in the rapid deflation position in which the rapid deflation port 16b is opened to rapidly deflate the cuff 10.

The CPU 24 is coupled via data bus to a ROM (read only memory) 26, a RAM (random access memory) 28 and an I/O (input/output) port 27, and processes the received signals according to programs pre-stored in the ROM 26 and by utilizing temporary-storage function of the RAM 28. The CPU 24 generates ON/OFF signal to a drive circuit 31 connected to the electric pump 18, so as to control application of electric power to the pump 18 through the drive circuit 31. Thus, activation and deactivation of the electric pump 18 is controlled by the CPU 24 via the drive circuit 31. Also, the CPU 24 generates command signal to the directional control valve 16 so as to selectively place the control valve 16 in one of the above-described three positions and thereby increase and decrease cuff pressure P. Further, the CPU 24 effects a series of operations for blood pressure measurement, based on pulse sound signal SO and cuff pressure signal SP. Specifically, the CPU 24 determines as maximum blood pressure cuff pressure P when the microphone 12 detects a Korotkoff sound for the first time in a current cycle, namely, when the Korotkoff sounds "appear", and as minimum blood pressure cuff pressure P when the Korotkoff sounds become unable to be detected by the microphone 12, namely, when the Korotkoff sounds "disappear", and generates display signal to a display device 29 through the I/O port 27 so as to display the determined maximum and minimum blood pressure.

The display device 29 has a cathode-ray tube for consecutively or continuously displaying a plurality of bars 25 in a two dimensional graph provided thereon, the two dimensional graph having an axis of abscissa 21 indicative of time and an axis of ordinate 23 indicative of blood pressure (mmHg) as shown in FIG. 2. An upper end A and a lower end B of each of the bars 25 correspond to maximum and minimum blood pressure of the subject, respectively.

A pulse wave sensor 32 is coupled to the CPU 24 via an A/D converter 34. As shown in FIG. 3, the pulse wave sensor 32 is secured to a band member 36 having a pair of slide fasteners (not shown) at opposite ends thereof. The pulse wave sensor 32 is set on a body surface over a radius near a wrist of the subject where pulse wave is comparatively easily detected. The band member 36 is wound around the wrist and the pair of slide fasteners are fastened, whereby the pulse wave sensor 32 is pressed locally against a radial artery extending near the radius, via the body surface over the artery, with a suitable pressing force ranging from 10 to 100 mmHg. The pulse wave sensor 32 detects pulse wave produced from the radial artery synchronously with heartbeat of the subject, and generates pulse wave signal SM representing the detected pulse wave to the CPU 24 via the A/D converter 34. The pulse wave sensor 32 includes a semiconductor strain gauge or a piezoelectric element for converting pulsation of the artery to electric signal, the electric signal being used as pulse wave signal. In the present embodiment, the pulse wave sensor 32 is set on the wrist of a free arm different from the arm on which the cuff 10 is set.

A clock signal generator 38 is coupled to the CPU 24, and generates pulse signal CK at a predetermined frequency.

Figure 4:
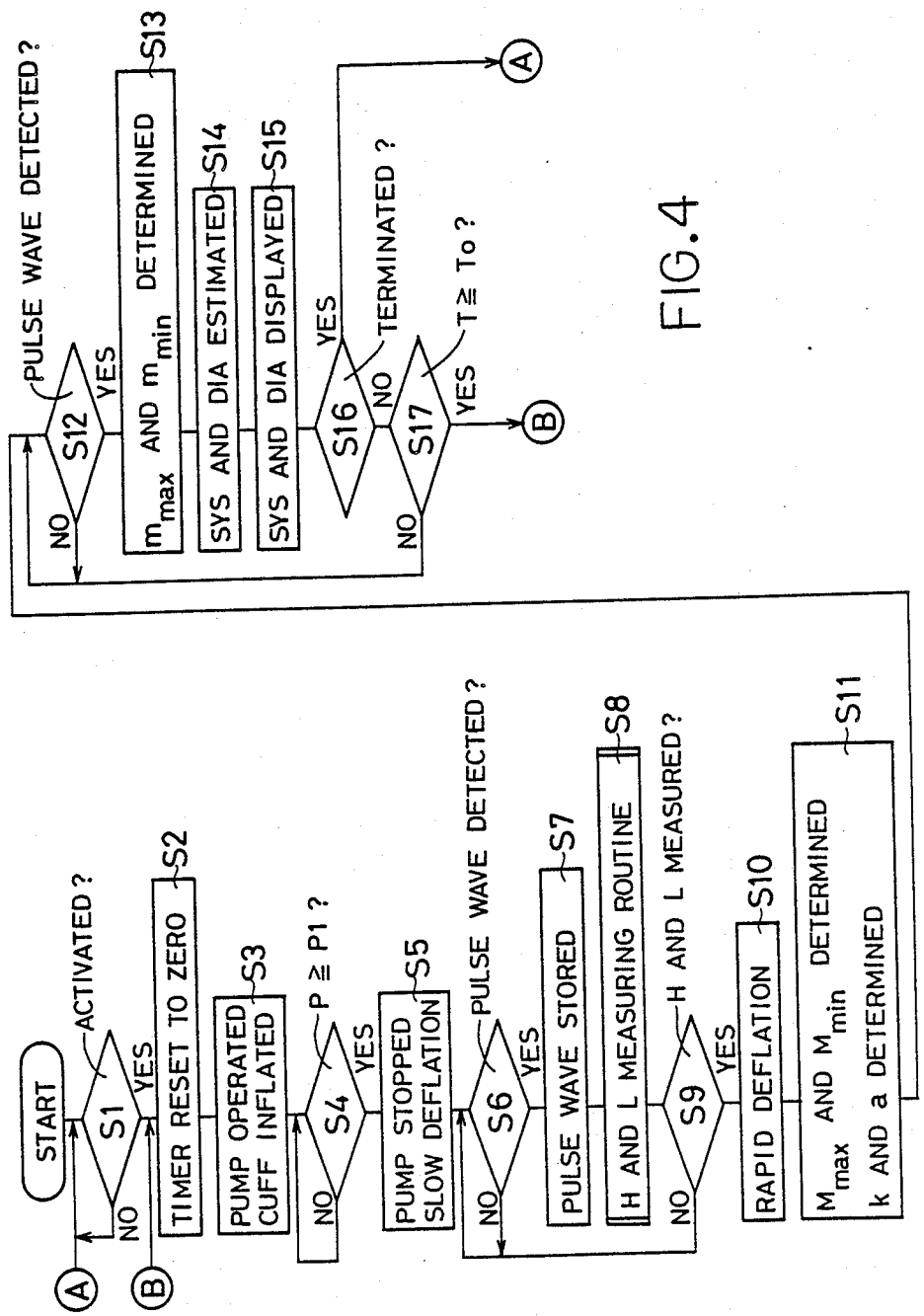
FIG. 4 is a flow chart illustrating the operation of the apparatus of FIG. 1.

Referring next to FIG. 4, there is illustrated the flow chart according to which the blood pressure monitoring apparatus constructed as described above is operated.

Upon application of electric power to the present apparatus as a result of operation of a power switch (not shown), the control of the CPU 24 goes to step S1 at which it is judged whether or not an ON/OFF switch (not shown) has been operated, namely whether or not activation signal is supplied from the ON/OFF switch to the CPU 24. In the case where the ON/OFF switch has been operated and activation signal is present at the CPU 24 after the inflatable cuff 10 is wound around the upper arm of the subject, the judgment at step S1 is affirmative (YES). While activation signal is not present at the CPU 24, step S1 is repeated until the judgment at step S1 is turned to be affirmative. Once the judgment at step S1 is affirmative, step S1 is followed by step S2 at which content or count T of a timer given in the form of software program is reset to zero so that then the timer re-starts counting a number of pulses of signal CK supplied from the clock signal generator 38. Step S2 is followed by step S3 at which the directional control valve 16 is placed in the inflation position so that pressurized fluid is supplied from the electric pump 18 to the cuff 10. Thus, cuff pressure P is increased. At the following step S4 it is judged whether or not cuff pressure P has reached a target pressure level P1, for example 180 mmHg, which is predetermined to be higher than estimated maximum blood pressure of the subject. If cuff pressure P has reached the target pressure level P1, step S4 is followed by step S5 at which the electric pump 18 is deactivated and the directional control valve 16 is switched from the inflation position to the slow deflation position, so that cuff pressure P is slowly decreased.

Step S5 is followed by step S6 at which it is judged whether or not pulse wave has been detected by the pulse wave sensor 32. If the judgement at step S6 is negative (NO), step S6 is repeated until pulse wave is detected. Meanwhile, if the judgement at step S6 is turned to be affirmative, step S6 is followed by step S7 at which the detected pulse wave consisting of a plurality of pulses are stored in order in the RAM 28.

Subsequently step S7 is followed by step S8, namely, a blood pressure measuring subroutine. At step 8 actual maximum blood pressure H (mmHg) and actual minimum blood pressure L (mmHg) are measured based on cuff pressure P at the times of the "appearing" and "disappearing" of the Korotkoff sounds, respectively, which times are represented by pulse sound signal SO, and the determined values H and L are stored in the RAM 28.

Step S8 is followed by step S9 at which it is judged whether or not maximum and minimum blood pressure H, L have been determined. If the judgement at step S9 is affirmative, step S9 is followed by step S10 at which the directional control valve 16 is switched from the slow deflation position to the rapid deflation position, so that cuff pressure P is rapidly decreased. On the other hand, the judgement at step S9 is negative, the control of the CPU 24 returns to step S6 and the following steps.

At the following step S11 the CPU 24 selects, from the plurality of pulses of the pulse wave stored in the RAM 28, a pair of pulses, $M_H$ and $M_L$ detected at the times of the "appearing" and "disappearing" of the Korotokoff sounds, respectively. Thus, the selected pulses $M_H$, $M_L$ correspond to the maximum and minimum blood pressure H, L, respectively. At step S11 also are determined a maximum magnitude $M_{max}$ of the selected pulse $M_H$ and a minimum magnitude $M_{min}$ of the selected pulse $M_L$, and the following equations (1) and (2) are determined based on values $M_{max}$, $M_{min}$:

$$SYS = K \cdot M_{max} + a \qquad (1)$$

$$DIA = K \cdot M_{min} + a \qquad (2)$$

wherein
SYS: maximum blood pressure,
DIA: minimum blood pressure, and
K, a: constants.

Constant K, a are determined by replacing values SYS, DIA with actual maximum and minimum blood pressure H, L, respectively. The thus determined equations (1), (2) are utilized at steps S12 through S14 for estimating maximum and minimum blood pressure SYS and DIA based on a maximum and a minimum magnitude $m_{max}$, $m_{min}$ of each of pulses of the pulse wave detected by the pulse wave sensor 32, respectively. In the present embodiment, the pair of equations (1), (2) correspond to the relationship between pulse wave magnitude and blood pressure (hereinafter, referred to as PW-BP relationship). The pair of equations (1), (2) are determined and utilized on the assumption that maximum and minimum blood pressure is in a proportional relation with a maximum and a minimum magnitude of each of pulses of the pulse wave, respectively. If a straight line represented by the pair of equations (1), (2) is drawn in a two dimensional graph having an x axis indicative of pulse wave magnitude and a y axis indicative of blood pressure, constants K and a correspond to the slope and y intercept of the straight line, respectively. Due to the y intercept a, the blood pressure does not always take zero mmHg even when the pulse wave magnitude takes zero.

Step S11 is followed by step S12 at which it is judged whether or not a pulse M1 of the pulse wave has been detected after the determination of the pair of equations (1), (2) at step S11. If the judgement at step S12 is affirmative, step S12 is followed by step S13 at which the CPU 24 reads in pulse M1, and determines a maximum magnitude $m_{max}$ and a minimum magnitude min of pulse M1 Step S13 is followed by step S14 at which the CPU 24 estimates maximum and minimum blood pressure SYS, DIA regarding pulse M1, by replacing values $M_{max}$, $M_{min}$ in the equations (1), (2) with values $m_{max}$, $m_{min}$, respectively. At the following step S15 the CPU 24 commands the display 29 to display a bar 25 representing the estimated values SYS, DIA at the upper and lower ends A, B, respectively.

Step 15 is followed by step S16 at which it is judged whether or not the ON/OFF switch has been operated again. If the judgement at step S16 is affirmative, the control of the CPU 24 returns to step S1. On the other hand, if otherwise, step S16 is followed by step S17 at which it is judged whether or not count T of the timer is incremented to a predetermined value T0. Value T0 corresponds to a regular time interval between each pair of consecutive two blood pressure measurements each of which is effected by inflating and deflating the cuff 10 and detecting Korotkoff sounds with the microphone 12 during the slow cuff deflation period for measuring actual maximum and minimum blood pressure H, L. Thus, the pair of equations (1), (2), namely, constants K, a are repetitively determined at the regular time intervals TO, such that a pair of equations (1), (2) determined at a current cycle are replaced with another pair of equations (1), (2) determined at the following cycle. Value TO is predetermined to fall within the range from 5 to 10 minutes. If the judgement at step S17 is negative, the control of the CPU 24 goes back to step S12 and the following steps, so as to read in pulses M2, M3, ... detected after pulse M1, estimate maximum and minimum blood pressure SYS, DIA of each pulse M2, M3, ..., and command the display device 29 to continuously display the estimated values SYS, DIA in the form of bars 25.

If the judgement at step S17 is turned to be affirmative while steps S12 through S16 are repeated, namely if count T of the timer is incremented to the predetermined value TO, the control of the CPU 24 returns to step S2 and the following steps. Specifically, at step S8 another pair of actual maximum and minimum blood pressure H, L are measured, and step S11 another pair of constants K, a of the equations (1), (2) are determined based on newly measured values H, L and a maximum magnitude $M_{max}$ of a pulse $M_H$ and a minimum magnitude $M_{min}$ of a pulse $M_L$ which pulses correspond to the newly measured values H, L, respectively. At steps 13 and 14 maximum and minimum blood pressure SYS, DIA are estimated based on a maximum and a minimum magnitude $m_{max}$, $m_{min}$ of each of the pulses of the pulse wave detected through the pulse wave sensor 32, according to the updated pair of equations (1), (2). And at step S15 the estimated maximum and minimum blood pressure are continuously displayed in the form of bars 25 on the display device 29.

Thus, in the present embodiment, step S11 stored in the form of software program in the ROM 26 and the CPU 24 and the RAM 28 for effecting step S11, serve as the means for repetitively determining the PW-B relationship (relationship between pulse wave magnitude and blood pressure), and replacing each of the repetitively determined PW-BP relationships with another PW-BP relationship determined next to the each of the repetitively determined PW-BP relationships. Meanwhile, steps S13, S14 stored in the ROM 26 and the CPU 24 and the RAM 28 for effecting those steps, serve as the means for continuously determining blood pressure based on magnitude of each of the pulses of the pulse wave continuously detected by the pulse wave sensor 32, according to a currently effective one of the repetitively determined PW-BP relationships.

As is apparent from the foregoing, in the present embodiment, blood pressure of the subject is continuously determined based on magnitude of each of the pulses of the continuously detected pulse wave, according to a currently effective one of the PW-BP relationships repetitively determined at the respective actual blood pressure measurements, namely, at the regular time intervals T0, and the thus determined blood pressure is continuously displayed.

Furthermore, in the present embodiment, the PW-BP relationship is updated, each time actual blood pressure is measured, based on magnitude of a pulse detected at the very time of measurement of the actual blood pressure. Thus, accurate correspondence between pulse wave magnitude and blood pressure is advantageously maintained in the PW-BP relationship. This assures that blood pressure is accurately determined based on the magnitude of each of the pulses of the pulse wave detected by the pulse wave sensor 32.

In the present embodiment actual maximum and minimum blood pressure H, L are measured by the Korotkoff-sound method, namely, detecting the times of the "appearing" and "disappearing" of Korotkoff sounds through the microphone 12 during a slow cuff deflation period. In this method, maximum and minimum blood pressure are determined at substantially the same time when the Korotokoff sounds "appear" on the microphone 12 and "disappear" from the same 12, respectively. Thus, the PW-BP relationship is rapidly determined.

Accordingly, the present apparatus is capable of monitoring blood pressure of a subject simply by pressing a body portion of the subject at regular time intervals. This arrangement permits a continuous blood pressure monitoring to be effected for a long time with extremely reduced uncomfortable feeling and/or congestion with the subject, in contrast to the conventional monitoring apparatus adapted to continue to press a body portion of a subject with a comparatively high pressing force.

Moreover, in the present embodiment, maximum and minimum blood pressure of a subject is determined at each pulsation of an artery, namely, each heartbeat of the subject, and concurrently displayed on the display device. Thus, the present apparatus provides medically or clinically significant information.

In a modified form of the present apparatus, the flow chart of FIG. 4 further includes step S18 as illustrated in FIG. 5. Step 18 is provided between steps S13 and S14 of the flow chart of FIG. 5. At step S8 it is judged whether or not the PW-BP relationship expressed by the pair of equations (1), (2) determined at step S11, has been broken. If the judgement at step S18 is affirmative, the control of the CPU 24 returns to step S2 and the following steps so as to re-determine another pair of equations (1), (2) based on newly measured actual maximum and minimum blood pressure H, L and newly determined values $M_{max}$, $M_{min}$ of pulses $M_H$, $M_L$ of the pulse wave. Due to a comparatively large motion of the wrist of the subject where pulse wave is detected, or a comparatively large variation in peripheral resistance of the subject, the PW-BP relationship may be broken. Such motion of the wrist may result in a change in conditions under which the pulse wave sensor 32 is pressed against the radial artery from which the pulse wave sensor 32 detects the pulse wave, while such variation, in the peripheral resistance may result from an unusual constriction or expansion of the radial artery. The breakage of the PW-BP relationship is found through detection of an aberrant pulse of the pulse wave. A comparatively large motion of the wrist may result in, for example, that the amplitude of a pulse of the pulse wave, for example, the magnitude of a peak point of the pulse as measured from a reference line (e.g., zero volt line) changes more than 50% per a unit time (e.g., 5 seconds), or that a pulse of the pulse wave occurs more than 30% before or after a time estimated from the times of occurrence of the preceding pulses, and in such cases at step S18 it is judged that the pulse of the pulse wave is aberrant. Meanwhile, a comparatively large variation in the peripheral resistance may result in, for example, that the position of a notch N (FIG. 6) of a pulse of the pulse wave changes more than 30% as compared with that of a notch of the preceding pulse, the position being expressed by a ratio of value A of an upper peak point of the pulse as measured from the position of the notch N to value B of the notch N as measured from a lower peak point of the pulse, or that the rate of change, namely,; slope of a decreasing portion C subsequent to the notch N which portion C corresponds to a diastolic period, largely changes as compared with that of a portion C of the preceding pulse. Further, an aberrant pulse is found at step S18, if blood pressure determined based on a pulse of the pulse wave detected by the pulse sensor 32 according to a PW-BP relationship, is deviated more than 40 mmHg from the actual blood pressure based on which that PW-BP relationship is determined.

Figure 7:
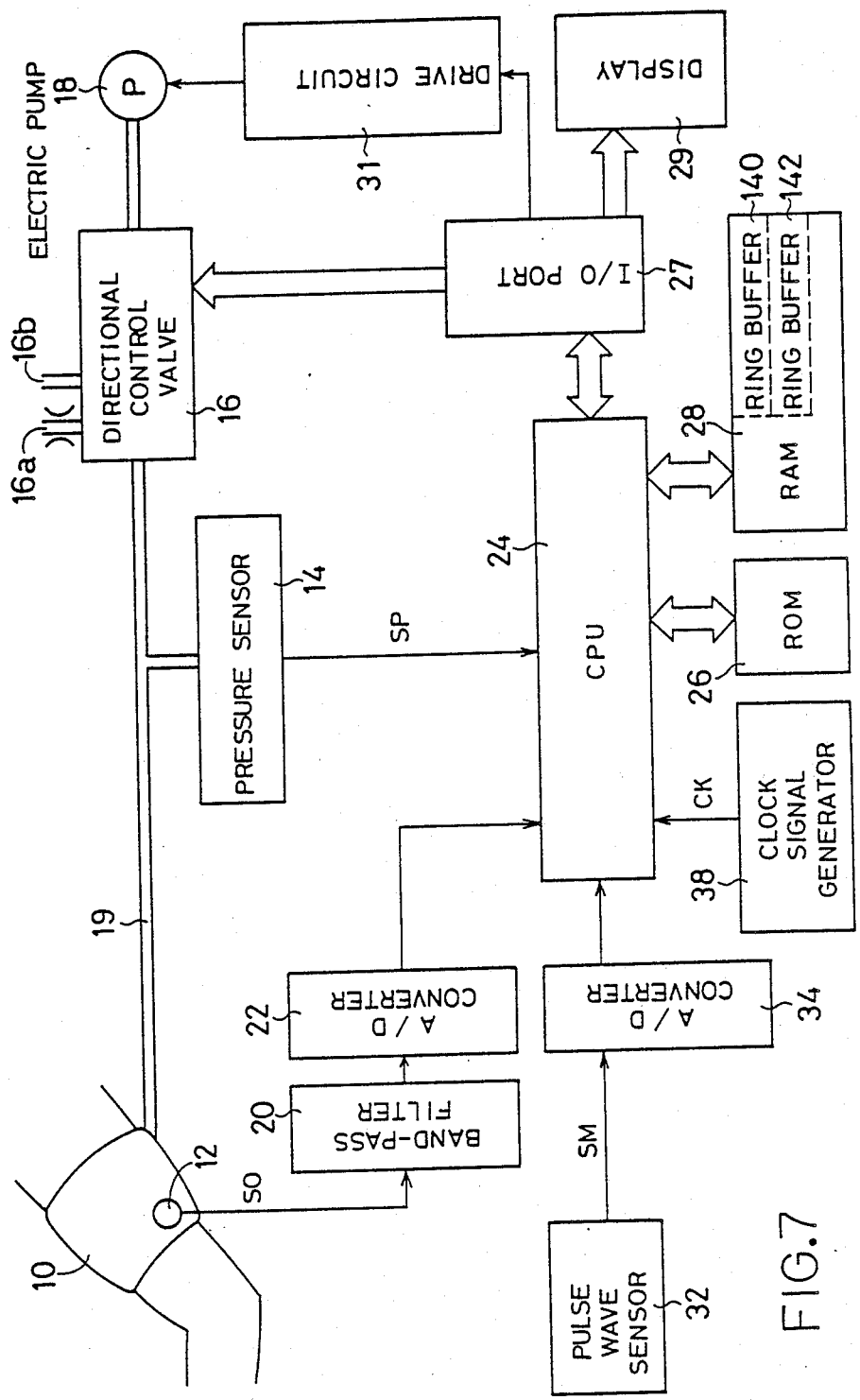
FIG. 7 is a diagrammatic view corresponding to FIG. 1, illustrating yet another embodiment of the apparatus of the invention.

Referring next to FIG. 7 there is illustrated another blood pressure monitoring apparatus embodying the present invention. The same reference numerals as used in FIG. 1 are used to designate corresponding elements or parts of the apparatus of FIG. 7, and repetitive description thereof will be omitted.

The instant apparatus is generally similar to the apparatus of FIG. 1, but is different in that, in the instant apparatus, a RAM 28 includes a first and a second ring buffer 140, 142. The first ring buffer 140 stores in order a predetermined number of pulses of the pulse wave which are detected by a pulse wave sensor 32 immediately before an inflatable cuff 10 is inflated to press an upper arm 11 of a subject. Meanwhile, the second ring buffer 142 stores in order a predetermined number of pulses of the pulse wave which are detected by the pulse wave sensor 32 after beginning of the inflation of the cuff 10. In the present embodiment, the number of the pulses stored in each of the first and second ring buffers 140, 142 is predetermined to be eight. Depending upon a judgement whether the pulse wave sensor 32 is on a peripheral or downstream side as viewed from the cuff 10 set around an arm 11 (hereinafter, referred to as cuff arm 11), or on a free arm (not shown) different from the cuff arm 11, the CPU 24 selects one pulse group from a first pulse group consisting of the eight pulses stored in the first ring buffer 140 and a second pulse group consisting of the eight pulses stored in the second ring buffer 142, so as to determine a PW-BP relationship (relationship between pulse wave magnitude and blood pressure) based on actual blood pressure and averages of magnitudes of the eight pulses of the selected pulse group. Specifically, if it is judged that the pulse wave sensor 32 is set over the arterial vessel on the downstream side of the cuff 10 on the cuff arm 11, the CPU 24 selects the first pulse group and determines the PW-BP relationship based on the selected first pulse group. If otherwise, namely, if it is judged that the pulse wave sensor 32 is set on the free arm different from the cuff arm 11, the CPU 24 selects the second pulse group and determines the PW-BP relationship based on the selected second pulse group. In the instant embodiment, the first ring buffer 140 serves as the first memory means for storing the pulses of the first pulse group, while the second ring buffer 142 serves as the second memory means for storing the pulses of the first and second pulse group. Eight pulses of each of the first and second pulse groups are generally equal to the number of pulses which are produced during two times of respiration of the subject, namely, a time length corresponding to twice a time period of respiration of the subject.

A clock pulse generator 38 generates pulse signal CK at a predetermined frequency, to the CPU 24.

Figure 8:
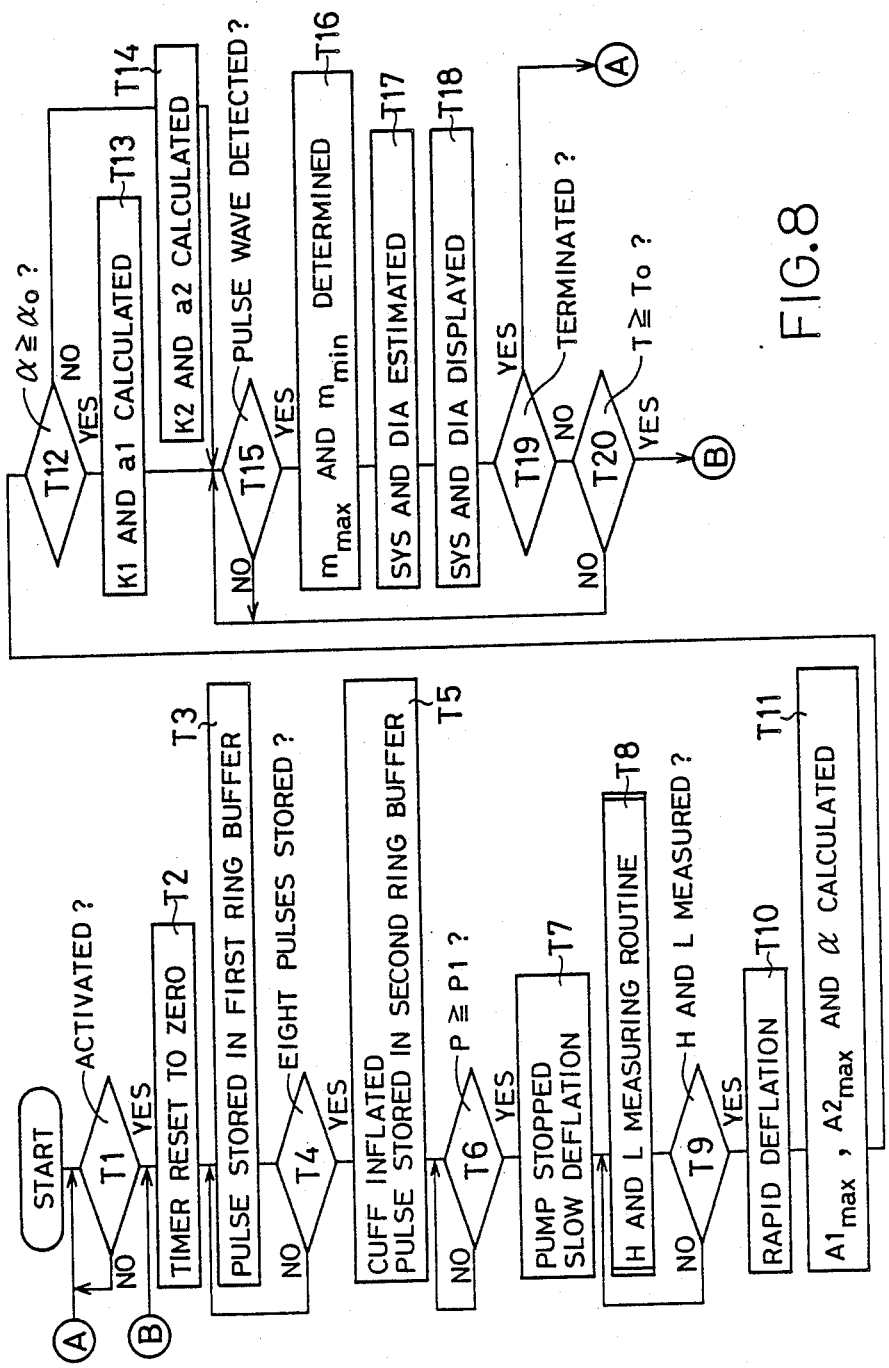
FIG. 8 is a flow chart corresponding to FIG. 5, illustrating the operation of the apparatus of FIG. 7.

Referring to FIG. 8 there is shown the flow chart according to which the instant blood pressure monitoring apparatus is operated.

Upon application of electric power to the instant apparatus as a result of operation of a power switch (not shown), the control of the CPU 24 goes to step T1 at which it is judged whether or not an ON/OFF switch (not shown) has been operated, namely, whether or not activation signal generated by the ON/OFF switch is present at the CPU 24. If the judgement at step T1 is affirmative (YES), step T1 is followed by step T2. Meanwhile, if activation signal is not present at the CPU 24 and the judgement at step T1 is negative (NO), step T1 is repeated until the judgement is turned to be affirmative. Once the judgement at step T1 is affirmative, step T1 is followed by step T2 at which count T of a timer given in the form of software program is reset to zero s that then the timer re-starts counting the number of pulses of pulse signal CK supplied from the clock signal generator 38 to the CPU 24.

Step T2 is followed by step T3 at which the first ring buffer 140 stores a pulse of the pulse wave which has been detected by the pulse wave sensor 32 and supplied in the form of pulse wave signal SM to the CPU 24. At the following step T4 it is judged whether or not the number of pulses stored in the first ring buffer 140 is increased to the above-described predetermined number, namely, eight. In other words the judgement at step T4 continues to be negative until the pulse wave sensor 32 has detected eight consecutive pulses of the pulse wave and the first ring buffer 140 stores the eight pulses, and the control of the CPU 24 repetitively returns to step T3 until the judgement at step T4 is turned to be affirmative. The eight pulses stored in the first ring buffer 140 constitutes the previously-described first pulse group. The first buffer 140 has eight elementary buffers and cannot store more than eight pulses. Consequently step T4 is followed by step T5.

At step T5 a directional control valve 16 is placed in an inflation position thereof in which the valve 16 permits an electric pump 18 to supply the cuff 10 with pressurized fluid, so that cuff pressure P in the cuff 10 is increased. Step T5 is followed by step T6 at which it is judged whether or not cuff pressure P has reached a target pressure level P1, for example 180 mmHg, which level is predetermined t be higher than estimated maximum blood pressure of the subject. Concurrently the second ring buffer 142 stores eight pulses of the pulse wave which are detected by the pulse wave sensor 32 immediately after beginning of the inflation of the cuff 10, namely, beginning of the pressing of the upper arm 11 with the cuff 10. The eight pulses stored in the second ring buffer 142 constitutes the previously described second pulse group. If cuff pressure P is increased to the target pressure level P1, step T6 is followed by step T7.

At step T7 the electric pump 18 is stopped and the control valve 16 is switched from the inflation position to a slow deflation position thereof in which the valve 16 permits the pressurized fluid in the cuff 10 to be slowly released through a slow deflation port 16a having a restrictor, so that cuff pressure P is slowly decreased. During the slow cuff deflation period, is effected step T8, a blood pressure measuring subroutine in which actual maximum blood pressure H (mmHg) and actual minimum blood pressure L (mmHg) of the subject are measured by detecting cuff pressure P (represented by cuff pressure signal SP supplied from a pressure sensor 14 to the CPU 24) at the times of "appearing" and "disappearing" of Korotkoff sounds (represented by pulse sound signal SO supplied from a microphone 12 to the CPU 24). The thus determined values H and L are stored in a RAM 28.

Step T8 is followed by step T9 at which it is judged whether or not values H and L have been measured. If the judgement at step T9 is affirmative, step T9 is followed by step T10 at which the control valve 16 is switched from the slow deflation position to a rapid deflation position in which the valve 16 permits the pressurized fluid in the cuff 10 to be rapidly released through a rapid deflation port 16b of the, valve 16, so that cuff pressure P is rapidly decreased. On the other hand, if the judgement at step T9 is negative, the control of the CPU 24 returns to step T8.

T10 is followed by step T11 at which are calculated an average $A1_{max}$ of maximum magnitudes of the eight pulses M1, M2, ..., M8 of the first pulse group (stored in the first ring buffer 140), and an average $A2_{max}$ of maximum magnitudes of the eight pulses m1, m2, ..., m8 of the second pulse group (stored in the second ring buffer 142). A difference is calculated by subtracting $A2_{max}$ from $A1_{max}$. At the following step T12 it is judged whether or not the difference $\alpha$ is more than a predetermined value $\alpha_o$. If the judgement at step T12 is affirmative, the CPU 24 makes an conclusion that the pulse wave sensor 32 is set on the cuff arm 11 (upper arm around which the cuff 10 is wound), and step T12 is followed by step T13. On the other hand, if the judgement is negative, the CPU 24 makes an conclusion that the pulse wave sensor 32 is set on the free arm different from the cuff arm 11, and step T12 is followed by step T14. In the case where the pulse wave sensor 32 is set on the downstream side of the cuff 10 on the cuff arm 11, if the cuff arm 11 is pressed under the inflated cuff 10, magnitude of the pulse wave detected while the cuff 10 is inflated is smaller more than the predetermined value $\alpha_o$ than that of the pulse wave detected before the cuff 10 is inflated. The reason for the fact is that, upon beginning of the pressing of the upper arm 11 by the inflated cuff 10, the pulse wave detected by the pulse wave sensor 32 becomes smaller and loses its normal wave form. The judgement at step T12 may be conducted by calculating an average of minimum magnitudes of the eight pulses of each of the first and second pulse groups and comparing those averages with each other.

If the judgement at step T12 is affirmative, namely, if it is judged that the pulse wave sensor 32 is set on the cuff arm 11, step T12 is followed by step T13 at which an average $A1_{min}$ of minimum magnitudes of the eight pulses $M_1, M_2, \ldots, M_8$ of the first pulse group (stored in the first ring buffer 140) is calculated, and the following equations (3), (4) are determined based on values $A1_{max}$ and $A1_{min}$:

$$SYS = K1 \cdot A1_{max} + a1 \quad (3)$$

$$DIA = K1 \cdot A1_{min} + a1 \quad (4)$$

wherein
SYS: maximum blood pressure,
DIA: minimum blood pressure, and
K1, a1: constants.

Constants K1, a1 are determined by replacing values SYS, DIA with actual maximum and minimum blood pressure H, L, respectively, measured at step T8. The pair of equations (3), (4) correspond to the PW-BP relationship, and are utilized at the following steps T15 through T17 for estimating maximum and minimum blood pressure SYS, DIA based on a maximum and a minimum magnitude $m_{max}$, $m_{min}$ of each of the pulses of the pulse wave detected by the pulse wave sensor 32, respectively. The pair of equations (3), (4) are determined and utilized on the assumption that maximum and minimum blood pressure SYS, DIA are in a proportional relation with a maximum and a minimum magnitude $m_{max}$, $m_{min}$ of a pulse of the pulse wave, respectively.

Meanwhile, if the judgement at step T12 is negative, namely, if it is judged that the pulse wave sensor 32 is set on the free arm different from the cuff arm 11, step T12 is followed by step T14 at which an average $A2_{min}$ of minimum magnitudes of the eight pulses m1, m2, ..., m8 of the second pulse group (stored in the second ring buffer 142), is calculated, and the following equations (5), (6) are determined based on values $A2_{max}$, $A2_{min}$, similarly to step T13:

$$SYS = K2 \cdot A2max + a2 \quad (5)$$

$$DIA = K2 \cdot A2min + a2 \quad (6)$$

wherein
SYS: maximum blood pressure,
DIA: minimum blood pressure, and
K2, a2: constants.

Constants K2, a2 are determined by replacing values SYS, DIA with actual maximum and minimum blood pressure H, L, respectively, similar to constants K1, a1 determined at step T13. The pair of equations (5), (6) correspond to the PW-BP relationship (relationship between pulse wave magnitude and blood pressure).

At the following step T15 it is judged whether or not a pulse N1 of the pulse wave has been detected after the determination of the pair of equations (3), (4) at step T13, or the determination of the pair of equations (5), (6) at step T14. If the judgement at step T15 is affirmative, step T15 is followed by step T16 at which a maximum magnitude $m_{max}$ and a minimum magnitude mmin of pulse N1 are determined. In the case where it has been judged at step T12 that the pulse wave sensor 32 is set on the cuff arm 11, namely, where the pair of equations (3), (4) have been established at step T13, maximum and minimum blood pressure SYS, DIA are estimated based on values $m_{max}$, $m_{min}$ of pulse N1 according to the equations (3), (4), respectively. Meanwhile, in the case where it has been judged at step T12 that the pulse wave sensor 32 is set on the free arm different from the cuff arm 11 and the equations (5), (6) have been established at step T14, values SYS, DIA are estimated based on values $m_{max}$, $m_{min}$ of pulse N1 according to the equations (5), (6), respectively.

Step T17 is followed by step T18 at which the estimated maximum and minimum blood pressure SYS, DIA is displayed on a display device 29.

Thus, in the instant embodiment, steps T12, T13 and T14 stored in the form of software program in the ROM 26 and the CPU 24 and the RAM 28 for effecting those steps, serve as the means for repetitively determining the PW-BP relationship, and replacing each of the repetitively determined PW-BP relationships with another PW-BP relationship determined subsequent to the each of the repetitively determined PW-BP relationships. Meanwhile, steps T16, T17 stored in the ROM 26 and the CPU 24 and the RAM 28 for effecting those steps, serve as the means for continuously determining blood pressure based on magnitude of each of the pulses of the pulse wave continuously detected by the pulse wave sensor, according to a currently effective one of the repetitively determined PW-BP relationships.

Step T18 is followed by step T19 at which it is judged whether or not the ON/OFF switch has been operated again. If the judgement at step T19 is affirmative, the control of the CPU 24 returns to step T1. On the other hand, if the judgement at step T19 is negative, step T19 is followed by step T20 at which it is judged whether or not count T of the timer is incremented to a predetermined value T0. Value T0 corresponds to a regular time interval between each pair of consecutive two blood pressure measurements each of which is conducted by inflating and deflating the cuff 10 and detecting Korotkoff sounds with the microphone 12, so as to measure actual maximum and minimum blood pressure H, L. Thus, the pair of equations (3), (4), or pair of equations (5), (6) are repetitively determined at the regular time intervals T0, and values SYS, DIA are determined based on values $m_{max}$, $m_{min}$ according to a currently effective one of the repetitively determined PW-PB relationships. In other words, a pair of equations (3), (4) or a pair of equations (5), (6) determined based on values H, L and values $A1_{max}$, $A1_{min}$ or values $A2_{max}$, $A2_{min}$ which are measured and determined at a current cycle, are replaced with another pair of equations (3), (4) or another pair of equations (5), (6) determined based on values H, L and values $A1_{max}$, $A1_{min}$ or values $A2_{max}$, $A2_{min}$ which are measured and determined at the following cycle. Value T0 is predetermined to fall in the range from 5 to 10 minutes.

If the judgement at step T20 is affirmative, the control of the CPU 24 returns to step T2. Meanwhile, if the judgement at step T20 is negative, the control of the CPU 24 goes back to step T15 and the following steps, so as to read in pulses N2, N3, ... detected after pulse N1, estimate maximum and minimum blood pressure SYS, DIA based on maximum and minimum magnitude $m_{max}$, $m_{min}$ of each of pulses N2, N3, ..., and command the display device 29 to continuously display the estimated values SYS DIA.

If the judgement at step T20 is turned to be affirmative while steps T15 through T19 are repeatedly effected, namely, if count T of the timer is incremented to value T0, the control of the CPU 24 returns to step T2 and the following steps. Specifically, at step T8 another pair of actual maximum and minimum blood pressure H, L are measured, and step T11 another pair of values $A1_{max}$, $A2_{max}$ are calculated. Further, at step T13 or step T14 another pair of equations (3), (4) or equations (5), (6), namely, constants K1, a1 or constants K2, a2 are determined based on those values H, L and $A1_{max}$, $A1_{min}$ or $A2_{max}$, $A2_{min}$. At steps T16 and T17 maximum and minimum blood pressure SYS, DIA are estimated based on a maximum and a minimum magnitude $m_{max}$, $m_{min}$ of each of pulses of the pulse wave detected by the pulse wave sensor 32, according to the updated pair of equations (3), (4) or (5), (6). And at step T18 the estimated values SYS, DIA are continuously displayed on the display device 29.

As is apparent from the foregoing, in the instant blood pressure monitoring apparatus, the magnitude of the pulse wave detected before the beginning of the pressing of the upper arm 11 with the inflated cuff 10 and stored in the first ring buffer 140, and the magnitude of the pulse wave detected after the beginning of the pressing of the upper arm 11 with the inflated cuff 10 and stored in the second ring buffer 142, are compared with each other, so that it is judged whether the pulse wave sensor 32 is set on the cuff arm 11 (arm around which the cuff 10 is wound) and on the downstream side of the cuff 10, or on the free arm other than the cuff arm 11. Depending upon the judgement, is selected either one of the two manners for determining the PW-BP relationship. According to the relationship determined in the selected manner, blood pressure is consecutively determined based on magnitude of the pulse wave detected by the pulse wave sensor 32. Since the instant apparatus selects one of the first and second pulse groups detected before and after the beginning of the pressing of the cuff arm 11, respectively, the apparatus is capable of accurately determining the PW-BP relationship, irrespective of the positional relationships between the pulse wave sensor 32 and the cuff 10. Accordingly, the instant blood pressure monitoring apparatus permits accurate monitoring of blood pressure of the subject.

Further, in the instant apparatus, the PW-BP relationship is determined based on averages of magnitudes of the eight pulses of the pulse wave in combination with actually measured blood pressure H, L, and maximum and minimum blood pressure SYS, DIA are estimated, according to the determined PW-BP relationship, based on magnitude of the pulse wave detected after the determination of the PW-BP relationship. A time length required for detecting eight pulses of pulse wave is generally equal to a time length for two times of respiration of a human, namely, twice a time period of respiration of a human. Since, in the instant apparatus, the PW-BP relationship is based on the eight pulses detected during a time length longer than the time period of respiration of the subject, the relationship is free from influences of respiration of the subject. Thus, this arrangement leads to increasing the degree of accuracy of the determined blood pressure.

Moreover, the instant apparatus provides various advantages similar to those of the apparatus of FIG. 1. For example, the instant apparatus permits a long blood pressure monitoring with extremely reduced uncomfortable feelings and/or congestion with the subject, because the apparatus monitors blood pressure simply by pressing the arm by the inflated cuff 10 at regular intervals ranging from 5 to 10 minutes, as contrasted to the conventional apparatus adapted to continue to press with a comparatively high pressing force an arm or other body portion of a subject.

The instant apparatus may be adapted to further incorporate means for finding that the PW-BP relationship determined at step T13 or step T14 has been broken, similar to the apparatus of FIG. 1. In this case, a step similar to step S18 of the flow chart of FIG. 5, is inserted between steps T16 and T17 of the flow chart of FIG. 8, so as to detect an aberrant pulse indicating that the PW-BP relationship has been broken.

While in the embodiment of FIG. 7 the pulses detected before the beginning of the pressing of the upper arm 11 with the cuff 10, and the pulses detected after the beginning, are stored in the first and second ring buffer 140, 142 in the RAM 28, respectively, it is possible to provide in the RAM 28 a single ring buffer having a predetermined number (e.g., sixteen) of elementary buffers and use half the sixteen buffers as the first memory means for storing the pulses detected before the beginning of the pressing and the other half as the second memory means for storing the pulses detected after the beginning of the pressing.

In the embodiment of FIG. 7, once the PW-BP relationship (3), (4) or (5), (6) is established, maximum and minimum blood pressure SYS, DIA is determined, each time a pulse wave of the pulse is detected by the pulse wave sensor 32, based on magnitude of the detected pulse according to the established PW-BP relationship. In this case, it is possible to adapt the second ring buffer 142 to continue to store in order the pulses of the pulse wave even after the establishment of the PW-BP relationship, so that values SYS, DIA are continuously determined based on a pulse stored in the last elementary buffer of the second ring buffer 142.

While in the embodiment of FIG. 7 the number of pulses of the pulse wave stored in each of the first and second ring buffers 140, 142, is eight which generally corresponds to twice the number of pulses detected during a time period of respiration of a human, namely twice a time period of respiration, it is possible to adapt the first and second ring buffers to store three or four pulses which generally corresponds to the number of pulses detected during the respiration period. It is further possible to adapt the ring buffers to store more than eight pulses, but in such cases it is preferred that the number of pulses stored in the ring buffers be equal to the number of pulses detected during a time length equal to a multiple of the respiration period.

While in the embodiment of FIG. 7 the PW-BP relationship is determined based on averages of magnitudes of the eight pulses of the pulse wave, it is possible to determine the relationship based on a selected one of a single pulse $M_\alpha$ detected immediately before the beginning of the pressing of the cuff arm 11 and a single pulse $M_{62}$ detected after the beginning of the pressing and before or when actual blood pressure is measured. Specifically, in the case where the pulse wave sensor 32 is set on the cuff arm 11 on the downstream side of the cuff 10, the PW-BP relationship is determined based on a maximum and a minimum magnitude $m_{max}$, $m_{min}$ of pulse $M_\alpha$ in combination with actual blood pressure. Meanwhile, in the case where the pulse wave sensor 32 is set on the free arm different from the cuff arm 11, the relationship is determined based on a maximum and a minimum magnitude of pulse $M_{62}$ in combination with actual blood pressure.

While in the embodiment of FIG. 7 maximum and minimum blood pressure is estimated based on a maximum and a minimum magnitude $m_{max}$, $m_{min}$ of each of pulses of the pulse wave, it is possible to estimate the maximum and minimum blood pressure based on varying averages of values $m_{max}$, $m_{min}$ of a plurality of consecutive pulses (e.g., eight pulses) which are detected during a time length equal to a time period of respiration of a subject or a multiple time length of that period. In this case, the estimated blood pressure is more advantageously free from the influences of respiration of the subject, and more reliable blood pressure monitoring is assured.

While the present invention has been described in its presently preferred embodiments, it is to be understood that the invention may be embodied in various modified forms.

For example, while in the embodiments of FIGS. 1 and 7 both maximum and minimum blood pressure is continuously determined and displayed, it is possible to continuously determine and display only one of maximum and minimum blood pressure. Alternatively it is possible to continuously determine and display average blood pressure.

While in the embodiments of FIGS. 1 and 7 actual blood pressure is measured by the Korotkoff-sound method, the blood pressure may be measured by other methods such as "oscillometric" method in which actual maximum and minimum blood pressure is determined based on variation in magnitudes of pulses of pulse wave which variation is detected as cuff pressure is varied. Alternatively it is possible to measure actual maximum and minimum blood pressure by "ultrasonic" method in which the blood pressure is determined based on variation in magnitude of oscillation of the wall surface of an artery which variation is detected with ultrasonic wave as cuff pressure is varied.

Although in the illustrated embodiments actual blood pressure is measured as cuff pressure P is decreased, it is possible to measure the blood pressure as the cuff pressure P is increased.

In the illustrated embodiments pulse wave is detected from a radial artery extending near a wrist of a subject, it is possible to set the pulse wave sensor over other arteries which extend near a body surface of a subject where the pulse wave is comparatively easily detected; such as a cartid artery, a dorsal pedal artery or a finger artery. In the case of the embodiment of FIG. 7, if the pulse wave sensor is not set on the cuff arm 11 on the downstream side of the cuff 10, the judgement at step T12 of FIG. 8 is negative (NO).

While in the illustrated embodiments of FIGS. 1 and 7 pulse wave is detected by the pulse wave sensor 32 set over the radial artery near the wrist of the subject with the help of the band 36 and pressed against the radial artery with a suitable pressing force, the pulse wave may be detected by a pulse wave detecting device shown in FIG. 9. The pulse wave detecting device includes a small inflatable cuff 240 which is set around a finger of the subject. The cuff 240 is supplied with pressurized fluid from an electrically operated pump 242 so that pressure in the cuff 240 is increased to a predetermined pressure level. The device further includes a pressure sensor 246 connected to the cuff 240 via a fluid piping 244. The pressure sensor 246 detects, as pulse wave, pressure oscillation (pressure variation) produced in the cuff 240 synchronously with heartbeat of the subject, and generates to the CPU 24 pulse wave signal representing the detected pulse wave. The pulse wave detecting device further includes a pressure regulating valve 248 disposed between the electric pump 242 and the cuff 240. The valve 248 is operated under control of the CPU 24 to regulate supply of the pressurized fluid from the pump 242 to the cuff 240 via the piping 244. Based on variation in magnitude (e.g., amplitude or power) of pulse wave signal supplied from the pressure sensor 246, it is judged whether or not the magnitude has been saturated. If the judgement is affirmative, the CPU 24 controls the pressure regulating valve 248 to maintain the cuff pressure at that level. This is a sort of feed-back control. Alternatively it is possible to adapt the CPU and the pressure regulating valve to maintain the cuff pressure at a predetermined level.

Further, the pulse wave sensor 32 and the band 36 employed in the illustrated embodiments may be replaced with a pulse wave detecting device including a housing, a rubber diaphragm defining a fluid-tight space in the housing, and a pressure sensor supported on an outer surface of the diaphragm. In this case, the housing is set on a body surface of a subject such that the diaphragm and pressure sensor are positioned right above an arterial vessel of the subject. Upon supply of pressurized fluid to the air-tight space of the housing through, for example, a pressure regulating valve, the diaphragm is inflated and the pressure sensor is pressed under the diaphragm against the arterial vessel with a suitable pressing force, so that the pressure sensor detects pulse wave produced from the arterial vessel. If the diaphragm is supported by the housing in a manner in which, when the diaphragm is inflated by the pressurized fluid fed thereto, only the diaphragm contacts the body surface and the housing does not contact the body surface, pressure oscillation corresponding to the pulse wave may be detected, via the diaphragm and the pressurized fluid, by a pressure sensor disposed in the air-tight space, on the housing, or apart from the housing.

Pulse wave may be detected by another type of detecting device including a pair of electrodes which are se at two positions apart from each other on a body surface (e.g., a finger) of a subject and between which a small electric current is applied, and a detector for detecting variation in impedance between the two positions which variation corresponds to the pulse wave.

Further, pulse wave may be detected by still another sort of detecting device including a light emitter for emitting a light beam to a body portion of a comparatively small thickness (e.g., a finger), and a light detector disposed opposed to the light emitter for detecting the light beam transmitted through an artery extending in the body portion. In this device, the pulse wave is detected based on variation in wavelength of the light beam detected by the light detector.

If each of the above-described various pulse wave detecting devices is used with the apparatus of FIG. 1, it is preferred that the device be set on the free arm different from the cuff arm 11 around which the cuff is wound. Meanwhile, if each pulse wave detecting device is used with the apparatus of FIG. 7, the apparatus is capable of judging whether the device is set on the cuff arm or the free arm different from the cuff arm, and selecting one of the first and second pulse groups stored in the first and second ring buffers 140, 142 depending upon the judgement.

While in the illustrated embodiments of FIGS. 1 and 7 the PW-BP relationship (relationship between pulse wave magnitude and blood pressure) is determined on the assumption that blood pressure is in direct proportion with pulse wave magnitude, namely, that blood pressure is expressed as a linear function of pulse wave magnitude, it is possible to assume that blood pressure is a quadratic function of pulse wave magnitude and determine the PW-BP relationship on that assumption. Alternatively the PW-BP relationship may be determined by preparing a plurality of data maps each representing a relationship between pulse wave magnitude and blood pressure and selecting one of the data maps based on the actually measured blood pressure and pulse wave magnitude of a subject.

Although in the illustrated embodiments the PW-BP relationship is defined by both the slope and y intercept of the pair of equations (1) and (2), (3) and (4) or (5) and (6), it is possible to define the PW-BP relationship by only the slope. In this case, the PW-BP relationship may be expressed by a pair of equations defined by a pair of different slopes, respectively, which are determined on the assumption that the proportional relationship between maximum blood pressure and a maximum magnitude of pulse wave is different from that between minimum blood pressure and a minimum magnitude of pulse wave.

While in the illustrated embodiments maximum and minimum blood pressure is continuously displayed on the cathode-ray tube of the display device, it is possible to concurrently record the blood pressure on a chart sheet or other sorts of recording sheets. The continuously determined blood pressure may be stored in an exclusive memory means such as a floppy.

It is to be understood that the present invention may be embodied with other modifications, improvements and changes that may occur to those skilled in the art without departing from the spirit and scope of the invention defined in the appended claims.

What is claimed is:

1. A method of monitoring blood pressure of a subject, the method comprising the steps of:
   (a) continuously detecting pulse wave which is produced from an arterial vessel of a subject synchronously with heartbeat of said subject, said pulse wave consisting of a plurality of pulses,
   (b) measuring at least one blood pressure of said subject by inflating an inflatable cuff set on a body portion of said subject so as to press said body portion, and subsequently deflating said inflatable cuff,
   (c) selecting one of a first pulse group consisting of at least one pulse of the pulse wave detected during a first time period immediately before beginning of the inflation of said inflatable cuff, and a second pulse group consisting of at least one pulse of the pulse wave detected during a second time period following said first time period, such that said first pulse group is selected if a magnitude of the at least one pulse of said second pulse group is smaller more than a predetermined value than a magnitude of the at least one pulse of said first pulse group, and such that said second pulse group is selected if said magnitude of said at least one pulse of said second pulse group is not smaller more than said predetermined value than said magnitude of said at least one pulse of said first pulse group,
   (d) determining a relationship between blood pressure and magnitude of pulse wave, based on the measured at least one blood pressure and at least one magnitude of the at least one pulse of the selected one of said first and second pulse groups,
   (e) repeating the above steps (b) to (d) and thereby updating the relationship between blood pressure and magnitude of pulse wave, and
   (f) continuously determining blood pressures of said subject based on magnitudes of the pulses of the continuously detected pulse wave, according to a currently effective one of the repetitively updated relationships.

2. The method as set forth in claim 1, wherein the step (e) consists of repeating the steps (b) to (d) and thereby updating said relationship at regular time intervals, the regular time interval falling in a range of 5 to 10 minutes.

3. The method as set forth in claim 1, wherein said second time period is equal to a time length required for inflating and deflating said inflatable cuff to measure the at least one blood pressure of the subject.

4. The method as set forth in claim 1, wherein each of said first and second time periods is equal to a multiple time length of a time period of respiration of said subject.

5. The method as set forth in claim 1, wherein the at least one pulse of each of said first and second pulse groups consists of eight pulses.

6. The method as set forth in claim 1, wherein said relationship is expressed as follows:

$$BP = K \cdot M + a$$

wherein
BP: blood pressure,
M: magnitude of pulse wave, and
K, a: constants.

7. The method as set forth in claim 1, wherein the step (b) consists of measuring a maximum and a minimum blood pressure of said subject, the step (d) consisting of determining said relationship based on the measured maximum and minimum blood pressure and a maximum and a minimum magnitude of the at least one pulse of said selected one pulse group, the step (f) consisting of determining a maximum and a minimum blood pressure of the subject based on a maximum and a minimum magnitude of each of the pulses of said pulse wave according to said currently effective relationship.

8. The method as set forth in claim 7, wherein the at least one pulse of each of said first and second pulse groups consists of eight pulses, said relationship being determined based on the measured maximum and minimum blood pressures and a pair of averages of maximum magnitudes and minimum magnitudes of said eight pulses of the selected one of said first and second pulse groups.

9. An apparatus for monitoring blood pressure of a subject, the apparatus comprising:
pulse wave detecting means for continuously detecting pulse wave which is produced from an arterial vessel of a subject synchronous with heartbeat of said subject, said pulse wave consisting of a plurality of pulses;
blood pressure measuring means including an inflatable cuff which is set on a body portion of said subject, said means measuring at least one blood pressure of said subject by inflating said inflatable cuff so as to press said body portion, and subsequently deflating said inflatable cuff;
selecting means for selecting one of a first pulse group consisting of at least one pulse of the pulse wave detected during a first time period immediately before beginning of the inflation of said inflatable cuff, and a second pulse group consisting of at least one pulse of the pulse wave detected during a second time period following said first time period, such that said selecting means selects said first pulse group if a magnitude of said at least one pulse of said second pulse group is smaller more than a predetermined value than a magnitude of said at least one pulse of said first pulse group, and that said selecting means selects said second pulse group if said magnitude of said at least one pulse of said second pulse group is not smaller more than said predetermined value than said magnitude of said at least one pulse of said first pulse group;
first determining means for determining a relationship between blood pressure and magnitude of pulse wave, based on the measured at least one blood pressure and at least one magnitude of the at least one pulse of the selected one of said first and second pulse groups, .
said blood pressure measuring means, said selecting means and said first determining means being operated for repetitively updating the relationship between blood pressure and magnitude of pulse wave; and
second determining means for continuously determining blood pressures of said subject based on magnitudes of the pulses of the continuously detected pulse wave, according to a currently effective one of the repetitively updated relationships.

10. The apparatus as set forth in claim 9, wherein said blood pressure measuring means, said selecting means and said first determining means update said relationship at regular time intervals, the regular time interval falling in an a range of 5 to 10 minutes.

11. The apparatus as set forth in claim 9, further comprising
first memory means for storing said at least one pulse of said first pulse group detected in said first time period, and
second memory means for storing said at least one pulse of said second pulse group detected in said second time period.

12. The apparatus as set forth in claim 9, further comprising
means for judging that said currently effective relationship has been broken,
upon the judgement that the currently defective relationship has been broken, said blood pressure measuring means newly measuring at least one blood pressure of said subject and said first determining means replacing the broken relationship with another relationship determined based on the new at least one blood pressure and at least one magnitude of the at least one pulse of the pulse wave detected in the first time period immediately before the beginning of the inflation of said inflatable cuff for measuring said new at least one blood pressure, or at least one magnitude of the at least one pulse of the pulse wave detected in the second time period following said first time period.

13. The apparatus as set forth in claim 9, further comprising
display means for displaying the continuously determined blood pressures of said subject, along a time axis.

14. The apparatus as set forth in claim 9, wherein said relationship is expressed as follows:

$$BP = K \cdot M + a$$

wherein
BP: blood pressure,
M: magnitude of pulse wave, and
K, a: constants.

15. A method of monitoring blood pressure of a subject, comprising the steps of:
(a) detecting pulse wave which is produced from an arterial vessel of a subject in synchronization with heartbeat of the subject, the pulse wave consisting of a plurality of pulses,
(b) varying pressure in an inflatable cuff set on a body portion of the subject, so as to inflate and deflate the cuff and thereby press said body portion,
(c) measuring a maximum and a minimum blood pressure of the subject, by detecting an appearance and a disappearance of Korotkoff sounds as the pressure of said cuff is varied, (d) determining a maximum magnitude of a pulse of the pulse wave which pulse is detected when the pressure of said cuff is equal to the measured maximum blood pressure, and a minimum magnitude of a pulse of the pulse wave which pulse is detected when the pressure of said cuff is equal to the measured minimum blood pressure, (e) determining a relationship between blood pressure and magnitude of pulse wave, based on the measured maximum and minimum blood pressures and the determined maximum and minimum magnitudes, and (f) repeating the above steps (b) to (e) and thereby updating the relationship between blood pressure and magnitude of pulse wave, and (g) determining blood pressures of the subject based on magnitudes of the pulses of the pulse wave according to a currently effective one of the respectively updated relationships.

16. The method as set forth in claim 15, wherein the step (f) consists of repeating the steps (b) to (e) and thereby updating said relationship at regular time intervals, the regular time interval falling in a range of 5 to 10 minutes.

17. The method as set forth in claim 15, wherein said relationship is expressed as follows:

$$BP = K \cdot M + a$$

wherein
BP: blood pressure,
M: magnitude of pulse wave, and
K, a: constants.

18. The method as set forth in claim 15, wherein the step (g) consists of determining a maximum and a minimum blood pressure of the subject according to said relationship based on a maximum and minimum magnitudes of each of the pulses of the pulse wave.

19. The method as set forth in claim 15, wherein the step (c) consists of determining as a maximum blood pressure of the subject a pressure value of said inflatable cuff when the Korotkoff sounds appear, and as a minimum blood pressure of the subject a pressure value of the cuff when the Korotkoff sounds disappear, as said inflatable cuff is deflated by decreasing the pressure of the cuff.

20. An apparatus for monitoring blood pressure of a subject, comprising:

pulse wave detecting means for detecting pulse wave which is produced from an arterial vessel of a subject in synchronization with heartbeat of the subject, the pulse wave consisting of a plurality of pulses;

an inflatable cuff set on a body portion of the subject;

cuff pressure varying means for varying pressure in said inflatable cuff so as to inflate and deflate the cuff and thereby press said body portion;

blood pressure measuring means for measuring a maximum and a minimum blood pressure of the subject, by detecting an appearance and a disappearance of Korotkoff sounds as the pressure of said cuff is varied;

pulse magnitude determining means for determining a maximum magnitude of a pulse of the pulse wave which pulse is detected when the pressure of said cuff is equal to the measured maximum blood pressure, and a minimum magnitude of a pulse of the pulse wave which pulse is detected when the pressure of said cuff is equal to the measured minimum blood pressure;

first determining means for determining a relationship between blood pressure and magnitude of pulse wave, based on the measured maximum and minimum blood pressures and the determined maximum and minimum magnitudes, said cuff pressure varying means, said blood pressure determining means, said pulse magnitude determining means and said first determining means being operated for repetitively updating the relationship between blood pressure and magnitude of pulse wave; and second determining means for determining blood pressures of the subject based on magnitudes of the pulses of the pulse wave according to a currently effective one of the repetitively updated relationships.

21. The apparatus as set forth in claim 20, wherein said cuff pressure varying means, said blood pressure determining means, said pulse magnitude determining means and said first determining means update said relationship at regular time intervals, the regular time interval falling in a range of 5 to 10 minutes.

22. The apparatus as set forth in claim 20, wherein said relationship is expressed as follows:

$$BP = K \cdot M + a$$

wherein
BP: blood pressure
M: magnitude of pulse wave, and
K, a: constants.

23. The apparatus as set forth in claim 20, wherein said second determining means determines a maximum and a minimum blood pressure of the subject according to said relationship based on a maximum and a minimum magnitude of each of the pulses of the pulse wave.

24. The apparatus as set forth in claim 20, wherein said blood pressure measuring means determines as a maximum blood pressure of the subject a pressure value of said inflatable cuff when the Korotkoff sounds appear, and as a minimum blood pressure of the subject a pressure value of the cuff when the Korotkoff sounds disappear, as said inflatable cuff is deflated by decreasing the pressure of the cuff.

25. The apparatus as set forth in claim 20, further comprising display means for displaying the blood pressures determined by said second determining means.

* * * * *